United States Patent [19]

Horzewski et al.

[11] Patent Number: 4,748,982
[45] Date of Patent: Jun. 7, 1988

[54] REINFORCED BALLOON DILATATION CATHETER WITH SLITTED EXCHANGE SLEEVE AND METHOD

[75] Inventors: Michael J. Horzewski, Sunnyvale; Paul G. Yock, San Francisco, both of Calif.

[73] Assignee: Advanced Cardiovascular Systems, Inc., Mountain View, Calif.

[21] Appl. No.: 653

[22] Filed: Jan. 6, 1987

[51] Int. Cl.⁴ ............................................. A61M 29/02
[52] U.S. Cl. .................................. 128/344; 604/102; 604/160
[58] Field of Search ................ 128/344, 348.1, 325, 128/10; 604/96, 102, 110, 111, 160, 161

[56] References Cited

U.S. PATENT DOCUMENTS

| | | | |
|---|---|---|---|
| 871,474 | 11/1907 | Buckner | 604/102 |
| 3,769,981 | 11/1973 | McWhorter | 604/96 |
| 4,616,648 | 10/1986 | Simpson | 128/344 |
| 4,652,258 | 3/1987 | Drach | 604/96 |

*Primary Examiner*—C. Fred Rosenbaum
*Assistant Examiner*—Gene B. Kartchner
*Attorney, Agent, or Firm*—Fulwider, Patton, Rieber, Lee & Utecht

[57] ABSTRACT

Balloon dilatation catheter adapted to be utilized in connection with a guiding catheter and a guide wire. The catheter comprises a flexible elongate tubular member having proximal and distal extremities and having a lumen extending therethrough. An inflatable balloon is mounted on the distal extremity of the tubular member. The interior of the inflatable balloon is in communication with the lumen. A sleeve extends through the balloon and extends rearwardly from the balloon and alongside the lumen. The sleeve has a guidewire lumen extending therethrough. The guidewire lumen is adapted to receive a guide wire extending therethrough and extending rearwardly of the flexible elongate element into a region adjacent the proximal extremity of the proximal elongate element. The sleeve has a slit extending longitudinally of the same from the proximal extremity of the sleeve to a region adjacent the balloon permitting the guide wire to be removed therethrough.

21 Claims, 1 Drawing Sheet

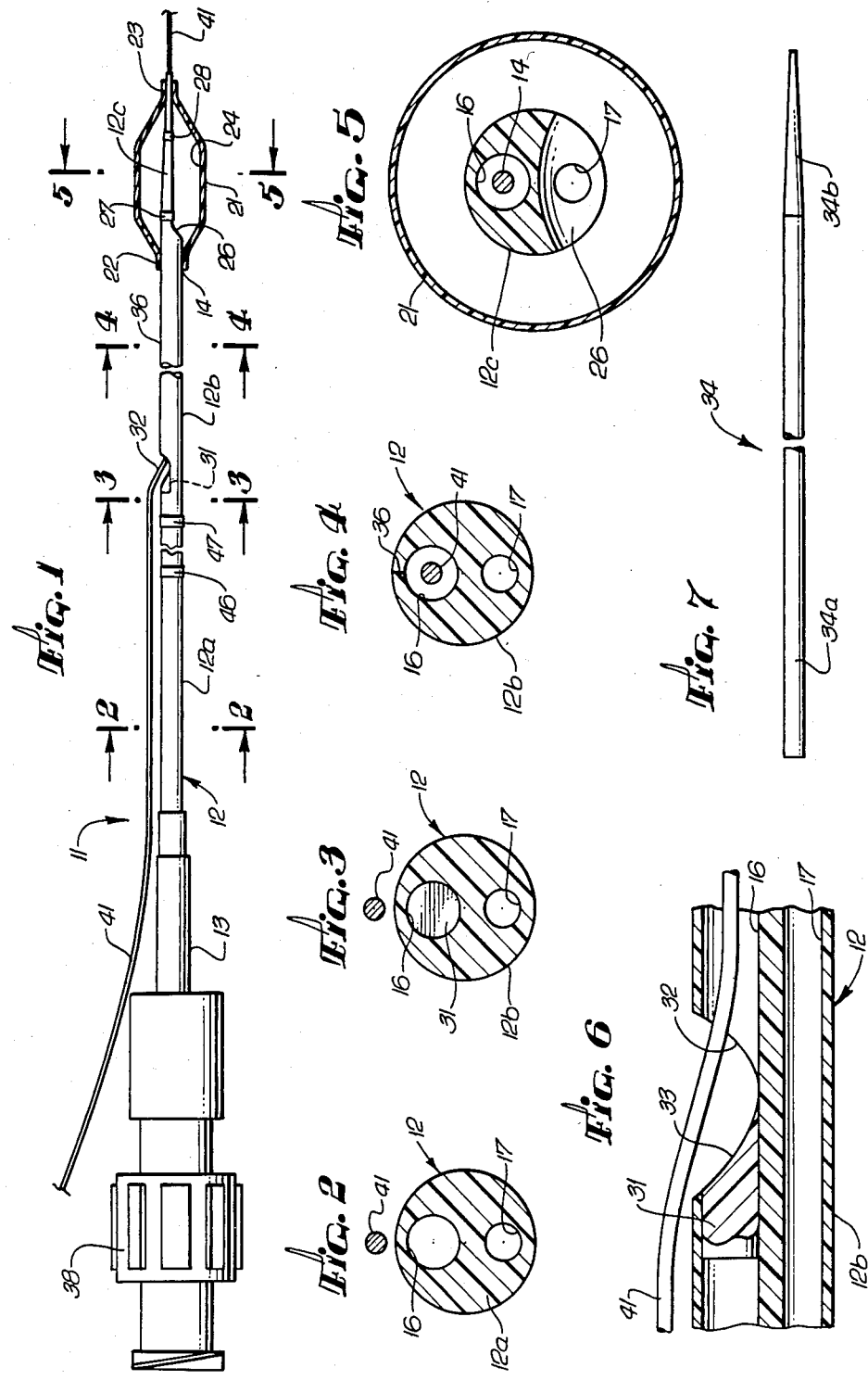

REINFORCED BALLOON DILATATION CATHETER WITH SLITTED EXCHANGE SLEEVE AND METHOD

This invention relates to balloon dilatation catheters and more particularly, to a reinforced balloon dilatation catheter having a slitted exchange sleeve and method.

In co-pending application Ser. No. 852,197, filed on Apr. 15, 1986, now abandoned entitled "Angioplasty Apparatus Facilitating Rapid Exchanges and Method", there is disclosed a balloon dilatation catheter which is provided with a sleeve adjacent its proximal extremity which is adapted to facilitate rapid exchanges of balloon dilatation catheters. In such balloon dilatation catheters, it has been found that there have been limitations in the control of the guide wire utilized therewith and in particular, its torqueability and its pushability in the catheter because the guide wire is freefloating through a substantial part of its length. In addition there was insufficient pushability in the balloon dilatation catheter itself. Also difficulties have been encountered making certain joints in the construction shown in the above-identified application. There is therefore a need for a new and improved balloon dilatation catheter which overcomes the above-named disadvantages.

In general, it is an object of the present invention to provide a balloon dilatation catheter which has been reinforced to increase its pushability.

Another object of the invention is to provide a balloon dilatation catheter and method of the above character which is provided with a slitted exchange sleeve to facilitate exchanges of balloon dilatation catheters.

Another object of the invention is to provide a balloon dilatation catheter of the above character in which the shaft of the dilatation catheter has varying degrees of stiffness to enhance pushability and trackability.

Another object of the invention is to provide a balloon dilatation catheter of the above character which has a stiff proximal portion, a soft distal portion and a very soft low profile tip portion.

Additional objects and features of the invention will appear from the following description in which the preferred embodiment is set forth in detail in conjunction with the accompanying drawings.

FIG. 1 is a cross-sectional side elevational view of a reinforced balloon dilatation catheter with slitted exchange sleeve incorporating the present invention.

FIG. 2 is a cross-sectional view taken along the line 2—2 of FIG. 1.

FIG. 3 is a cross-sectional view taken along the line 3—3 of FIG. 1.

FIG. 4 is a cross-sectional view taken along the line 4—4 of FIG. 1.

FIG. 5 is a cross-sectional view taken along the line 5—5 of FIG. 1.

FIG. 6 is an enlarged cross-sectional view of a portion of the catheter shown in FIG. 1.

FIG. 7 is a side elevational view of the reinforcing mandrel which is utilized in the device shown in FIG. 1.

In general, the reinforced balloon dilatation catheter with slitted exchange sleeve is adapted to be utilized with a guiding catheter inserted into the vessel of the patient. It is comprised of a flexible elongate member with its stiffness decreasing from the proximal extremity to the distal extremity. It is provided with the first and second lumens extending therethrough. Inflatable balloon means is provided. Means is provided for securing the inflatable balloon means to the distal extremity of the flexible elongate tubular member with the interior of the balloon being in communication with the second lumen. A plug is provided in the first lumen in a region which is spaced away from the balloon towards the proximal extremity of the flexible elongate tubular member. A notch is fored in the elongate flexible tubular member in the plug so that it opens up into the first lumen in the side of the plug proximal to the balloon. A guide wire is adapted to extend through the notch and through the first lumen so that it extends through the balloon and beyond the distal extremity of the balloon. The guide wire also extends rearwardly from the notch along the outside of the flexible tubular member beyond the proximal extremity of the flexible elongate tubular member. If desired the proximal extremity of the flexible elongate tubular member can be reinforced by placing a mandrel of a suitable material such as metal in the first lumen from the proximal extremity of the flexible tubular member up to the plug in the first lumen.

More in particular, as shown in the drawings, the reinforced balloon dilatation exchange catheter 11 with slitted exchange sleeve consists of a flexible elongate tubular member 12 which is provided with proximal and distal extremities 13 and 14 and which has first and second lumens 16 and 17 extending therethrough. The lumen 16 serves as a guide wire lumen whereas the lumen 17 serves as the balloon inflation lumen. As can be seen, the tubular member 12 in effect provides a dual lumen shaft. In order to achieve the desirable stiffness for the shaft, the tubular member 12 is formed so that it has varying degrees of stiffness with decreasing stiffness towards the distal extremity of the same. The tubular member 12 can be formed of a suitable material such as a polyolefin of various densities. By way of example, assuming that the tubular member 12 has a suitable length, as for example 135 centimeters, the first portion 12a of the tubular member 12 of a length of 105 centimeters from the proximal end can be extruded from a polyolefin compound having a high percentage of high density material, possibly even 100%, with an outside diameter of approximately 0.050 inches and with dual lumen or first and second lumens 16 and 17 having suitable dimensions as, for example, 0.02 inches for the first lumen which is to serve as a guide wire lumen and 0.012 inches for the second lumen which is to serve as a balloon inflation and deflation lumen. In the portion 12b of the tubular member 12 extending beyond the 105 centimeter portion, as for example, the remaining length of the tubular member, the tubular member is reduced to a smaller diameter, as for example, an outside diameter of approximately 0.044 inches and with the tubular member being extruded of a suitable material such as a mixture of a reduced percentage of high density and an increased percentage of low density polyolefin to provide a tubular member which is more flexible and better able to track the arterial vessel.

The formation of the tubular member 12 of different outside diameters and of materials having different stiffnesses can be readily accomplished by extruding the two portions in separate extrusions using the desired ratio of high density and low density materials. After the extruded portions have been formed, they can be joined together in a suitable manner such as by inserting two mandrels of appropriate sizes through the lumens 16 and 17 from the proximal extremity of the portion formed of a high percentage high density polyolefin and of the portion 12b formed of reduced percentage high density and increasd percentage low density polyolefin. After the mandrels (not shown) have been inserted, the abutting extremities of the portions 12a and 12b can be bonded together by suitable means such as by application of heat by the use of a heat gun to abutting extremities of the flexible tubular member. After the bond has been formed, the mandrels can be removed from the proximal extremity of the tubular member. In order to facilitate the heat bonding, a glass mold can be utilized for encasing the abutting extremities of tubular members while the bond is being made.

An inflatable balloon or inflatable balloon means 21 is provided which can have an inflated diameter of a suitable size, as for example, from 1.5 to 4.0 millimeters. The balloon 21 can be formed of a suitable material such as heat shrinkable polyolefin and is provided with necked down proximal and distal extremities 22 and 23. These proximal and distal extremities 22 and 23 are secured to the distal extremity portion 12c of the tubular member 12 so that the distal extremity of the tubular member 12 is in alignment with the distal extremity of the balloon 21. The proximal and distal extremities 22 and 23 can be secured to the tubular member 12 to form liquid-tight seals in a suitable manner such as by the use of an adhesive, or alternatively, by heat shrinking the same onto the tubular member 12 if the balloon 21 is formed of a heat shrinkable material. The interior 24 of the balloon 21 is in communication with the second lumen 17 through an opening or hole 26 provided in the tubular member 12 within the interior of the balloon.

Radiopaque marker means is provided in the form of radiopaque bands 27 and 28 which are secured to the tubular member 12 within the balloon 21 near the distal and proximal extremities of the balloon. Suitable material such as gold, tungsten or platinum may be utilized for the bands.

The distal portion 12c of the tubular member 12 is formed with a single or first lumen 16 and commences in the region just interiorally of the balloon 21 and can be formed of a suitable compound, such as polyolefin, of an appropriate mixture of high density and low density materials depending on the desired stiffness for this portion of the tubular member. The portion 12c can be bonded to the portion 12b in the manner hereinbefore described for bonding of portions 12b to 12a. By utilizing a single lumen for this portion of the tubular member, it is possible to reduce the outside diamter or profile of the tubular member to a suitable diameter such as 0.029 inches while retaining an inside diameter of 0.020 inches for the first lumen 17. This lower profile makes it possible to utilize smaller balloons.

In accordance with the present invention, a plug 31 of a suitable material such as polyolefin is inserted into the first lumen 16 from the distal extremity of the tubular member 12 into a region which is just distal of the junction between the portions 12a and 12b as shown particularly in FIGS. 1 and 6. This insertion can be accomplished by utilizing a mandral (not shown) and pushing the plug 31 to the desired position. In order to be able to visually observe the position of the plug 31 in the lumen 16, the plug 31 is preferably formed of a colored material. After the plug 31 has been moved to the desired position, heat is applied to that portion of the tubular member to blend the plug 31 to the inner wall of the tubular member forming the lumen 16 so that the lumen 16 is sealed off or occluded at that point. Alternatively, the plug 31 can be formed by placing two mandrels (not shown) in lumen 16 and providing a space between their innermost ends which approximates the length of the plug 31 desired. Another mandrel (not shown) is placed on the lumen 17 so that it extends through the region of the space between the two spaced apart mandrels in lumen 16. The portion of the tubular member containing the space is heated in a mold so that the plastic material forming the member will melt and flow into the space to form a plug 31 in the lumen 16. After cooling of that portion of the tubular member, the mandrels can be removed. Thereafter, a notch 32 is cut into the tubular member 12 so that it cuts into the distal extremity of the plug 31 and so that an opening is formed into the first lumen 16 distal of the plug 31 which opens exteriorally of the tubular member 12 and also to provide an inclined ramp 33.

If it is desired to provide additional stiffness in the proximal extremity of the tubular member 12, a mandrel 34 such as shown in FIG. 7 can be inserted into the portion of the lumen 16 proximal of the plug 31 to serve as a stiffener. The mandrel 34 can have suitable dimensions, as for example, a portion 34a continuous diameter of approximately 0.020 inches for approximately 98 centimeters of its length from its proximal extremity with a distal portion 34b having a continuous taper of 10 centimeters tapering down to a final dimension of approximately 0.012 inches. When such a mandrel 34 is utilized, the mandrel can be utilized for properly positioning the plug 31 in the first lumen 16 and can be left in place to serve as the stiffener. The mandrel 34 can be formed of a suitable material such as stainless steel. If the mandrel is to be used as a stiffener it is advised to flatten approximately 1 centimeter of the distal top of the mandrel 34 and locate this portion within the plug to secure the mandrel in place.

The sidewall of the tubular member 12 distal of the notch 32 is provided with a slit 36 extending longitudinally of the tubular member to a location which is approximately 0.5 to 1 centimeters from the proximal extremity of the balloon 21. This slit 36 extends down into the first lumen 16 throughout this portion of the tubular member 12.

A single lumen Luer-type adapter 38 is mounted on the proximal extremity of the tubular member 12 and is in communication with the second lumen 17.

A guide wire 41 of a suitable type such as the 0.018 "Hi-Torque Floppy" guide wire manufactured and sold by Advanced Cardiovascular Systems, Inc. of Mountain View, Calif. is utilized and can be inserted into the catheter 11 by taking the proximal extremity of the guide wire 41 and threading it into the first lumen 16 opening through the distal extremity of the catheter 11 and advancing it towards the proximal extremity of the catheter 11 until it engages the ramp 33 of the plug 31 and is ramped out through the notch 32. The guide wire 11 can then be grasped and pulled so that it extends longitudinally of the remaining portion of the tubular member 12 and so that it extends beyond the fitting 38.

Visual marking means is provided for locating the relative positions of a balloon dilatation catheter 11 of the present invention in a guiding catheter. For example, a proximal marker 46 can be placed a suitable distance as, for example, 106 centimeters from the distal tip of the catheter 11 to indicate in the angioplasty procedure when the distal tip of the dilatation catheter is at the distal tip of a guiding catheter. The marker 46 can be in the form of a thin sleeve, approximately 0.5 centimeters in length, of irradiated, colored 100% low density polyethylene. The sleeve forming the marker 46 can be heat shrunk onto the tubular member 12 as shown in FIG. 1. A similar marker 47 can be provided on the tubular member 12 just proximal of the notch 32 as shown in FIG. 1.

Operation and use of the balloon dilatation catheter 11 hereinbefore described may now be briefly described as follows. As explained in co-pending application Ser. No. 852,197 filed on Apr. 15, 1986, the guiding catheter is first inserted into the vessel of the patient. Thereafter, a balloon dilatation catheter 11 of the present invention of the appropriate size is selected and a guide wire 41 is introduced therein as hereinbefore described. The catheter 11 with its guide wire 41 can then be introduced into the guiding catheter in a conventional manner by first advancing the guide wire into the stenosis and thereafter advancing the balloon dilatation catheter so that the balloon 21 is in the stenosis. By providing a catheter shaft which is formed of various densities of a suitable material such as polyolefin and also by providing the mandrel-type stiffener 34 in the proximal extremity of the tubular member 12, the desired amount of stiffness can be readily obtained to achieve the desired pushability so that the catheter can be readily pushed, or advanced, into the desired location in the stenosis. In such a procedure it should be appreciated that the notch 32 is always positioned within the guiding catheter as is the portion of the guide wire outside of and free of the catheter 11 extending proximally of the notch 32 except where the catheter 11 extends out of the guiding catheter. Thus, the guide wire 41 and the notch 32 will never be outside of the guiding catheter during an angioplasty procedure.

Now let it be assumed that it is desired to exchange the dilation catheter herein described for a different dilatation catheter, as for example, one having a smaller balloon or alternatively a larger balloon. When this is the case, the guide wire 41 is retained in its position in the stenosis and the balloon dilatation catheter is removed by withdrawing the same until the notch 32 appears outside of the guiding catheter. Thereafter as the catheter 11 is withdrawn, the guide wire can be pulled out through the slit 36 until the catheter has been withdrawn into a point which is just proximal of the balloon 21. Thereafter, the catheter 11 can be withdrawn on the guide wire 41 until the balloon 21 clears the rotating hemostasis valve which is attached to the proximal end of the guiding catheter.

The catheter 11 is then removed from the guide wire. The other catheter which is desired to be used can be threaded onto the distal extremity of the guide wire 41 and then advanced through the rotating hemostatis valve over the guide wire which is still in position into the stenosis to accomplish a further dilation in a conventional manner.

With this procedure it can be seen that it has been possible to accomplish a rapid exchange of a dilatation catheter by merely making the exchange over a very short length, such as 3 cenitmeters of the guide wire. Thus with a catheter of the present invention it is possible to utilize conventional guide wires without the necessity for long exchange wires as has been the practice in the past. In addition, it has been possible to accomplish such an exchange utilizing a balloon dilatation catheter which still has the desired amount of stiffness to make it pushable into a remote stenosis.

It should be appreciated that in the present invention in place of the sleeve which was provided in application Ser. No. 852,197, filed on Apr. 15, 1986, a slitted sleeve has in effect been provided which still further reduced the distance over which an exchange must be accomplished.

What is claimed is:

1. A balloon dilation catheter adapted to be utilized with a guidewire comprising a flexible elongate tubular member having proximal and distal portions, a lumen extending therethrough, an inflatable balloon on the distal portion, the interior of the inflatable balloon being in communication with the lumen and a sleeve-like means having a proximal opening and extending through the balloon to a distal opening in the distal extremity of the tubular member, said sleeve-like means adapted to receive a guidewire therethrough and having a slit extending longitudinally from the proximal opening of the sleeve to a region adjacent the balloon facilitating removal of the guidewire therethrough.

2. A catheter as in claim 1 wherein said sleeve-like means is in the form of an additional lumen provided in the tubular member.

3. A catheter as in claim 1 wherein said tubular member has a portion thereof formed of a higher density material than other portions of the member to provide different stiffnesses for the tubular member.

4. A catheter as in claim 2 including an additional lumen which extends proximally from the proximal opening of the sleeve and wherein a stiffening means is disposed in the additional lumen in the tubular member.

5. A catheter as in claim 4 wherein said stiffening means is in the form of an additional member formed within the tubular member.

6. A catheter as in claim 5 wherein said stiffening means is in the form of a mandrel, at least a portion of which is tapered.

7. A catheter as in claim 1 together with visual marking means carried by the tubular member.

8. A catheter as in claim 6 wherein said marking means is colored.

9. A balloon dilatation catheter for use with a guidewire which is adapted to be inserted in a vessel of a patient comprising, a flexible elongate tubular member having proximal and distal portions and having first and second lumens extending therethrough, a balloon carried by the distal portion of the tubular member and having its interior in communication with the second lumen, the tubular member being provided with a sleeve which extends from a first opening in the exterior of the distal portion of the tubular member through the first lumen to a second opening in the tubular member distally of the balloon, the first opening being positioned proximally of the balloon and adapted to receive a guidewire which extends through the sleeve in the first lumen to the second opening, the said tubular member formed from plastic materials having various densities to provide a decreasing stiffness from the proximal portion to the distal portion.

10. A catheter as in claim 9 together with plug means disposed in the first lumen proximal of the first opening and serving as a ramp to urge the guidewire out of the first opening when the guidewire is threaded through the second opening into the first lumen.

11. A catheter as in claim 9 together with stiffener means disposed in the first lumen from the proximal extremity of the tubular member into a region adjacent the notch.

12. A catheter as in claim 9 wherein the sleeve is provided with a slit extending longitudinally of the tubular member from the first opening through the first lumen to a region adjacent the proximal end of the balloon.

13. A catheter as in claim 9 wherein portions of the tubular member are formed of a plastic of varying densities to provide decreasing stiffness along the length of the tubular member from the proximal portion to the distal portion thereof.

14. A catheter as in claim 13 wherein the proximal portion of the tubular member is formed of 100% high density plastic.

15. A catheter as in claim 14 wherein the tubular member includes an intermediate portion which is formed of a mixture of high density plastic and low density plastic.

16. A catheter as in claim 11 wherein said stiffener is in the form of a mandrel disposed in the first lumen.

17. A catheter as in claim 16 wherein the distal portion of the mandrel is tapered to vary the stiffness provided by the mandrel.

18. A catheter as in claim 17 wherein the mandrel is formed of a metal.

19. A catheter as in claim 9 together with colored visual marker means carried by the tubular member.

20. In a method for performing an angioplasty procedure in which a guiding catheter is disposed in the vessel of the patient and in which a balloon dilatation catheter with a guide wire disposed therein is inserted into the guiding catheter, the balloon dilatation catheter having an elongate flexible tubular member with sleeve-like means carried by the flexible tubular member, the sleeve-like means having a guide wire lumen extending therethrough which receives the guide wire, the sleeve-like means having a slit therein extending from the proximal extremity of the sleeve to a region adjacent the proximal extremity of the balloon of the balloon dilation catheter, the method including the steps of taking the proximal extremity of the guide wire, inserting it into the distal extremity of the sleeve-like means and pushing it rearwardly through the sleeve-like means until it exits from the sleeve-like means and then further advancing the guide wire so that the guide wire extends alongside of and exterior of substantially the entire remaining length of the flexible elongate tubular member, inserting the balloon dilatation catheter with the guide wire therein into the guiding catheter, advancing the guide wire into a stenosis, thereafter performing an angioplasty procedure with the balloon dilatation catheter, and removing the balloon dilatation catheter from the guide wire by leaving the guide wire in place by withdrawing the balloon dilatation catheter along the guide wire until the sleeve-like means, becomes visible exteriorally of the guiding catheter, thereafter further withdrawing the balloon dilatation catheter and removing the guide wire through the slit until the portion of the catheter having the slit therein is exposed exteriorally of the guiding catheter and thereafter removing the balloon dilatation catheter from the guide wire.

21. A method as in claim 10 together with the step of selecting another balloon dilatation catheter and positioning it so that the distal extremity of the sleeve-like means is positioned on the proximal extremity of the guide wire already disposed in the guiding catheter, advancing the selected catheter onto the guide wire until the guide wire exits from the sleeve-like means and then continuing to advance the catheter over the guide wire with the guide wire traveling exteriorally of the tubular member, continuing to advance the catheter until the balloon is near the distal extremity of the guide wire, performing an angioplasty procedure with the balloon dilatation catheter and thereafter removing the balloon dilatation catheter and the guide wire from the guiding catheter.

* * * * *